United States Patent [19]
Yuan et al.

[11] Patent Number: 5,352,225
[45] Date of Patent: Oct. 4, 1994

[54] DUAL-TIER SPINAL CLAMP LOCKING AND RETRIEVING SYSTEM

[76] Inventors: Hansen A. Yuan, 5066 Pine Valley Dr., Fayetteville, N.Y. 13066; Chih-I Lin, 813 S. Golden Pardos Dr., Diamond Bar, Calif. 10765

[21] Appl. No.: 4,610

[22] Filed: Jan. 14, 1993

[51] Int. Cl.⁵ ............................ A61H 7/00; A61F 2/44
[52] U.S. Cl. ........................................ 606/61; 623/17
[58] Field of Search ................ 623/16, 17; 606/61; 24/525

[56] References Cited

U.S. PATENT DOCUMENTS

| | | | |
|---|---|---|---|
| 2,611,637 | 9/1952 | Neswno | 24/525 |
| 4,279,248 | 7/1981 | Gabbay | 24/525 |
| 4,611,582 | 9/1986 | Duff | 606/61 |
| 5,167,662 | 12/1992 | Hayes et al. | 606/61 |

*Primary Examiner*—David Isabella
*Attorney, Agent, or Firm*—Bacon & Thomas

[57] ABSTRACT

A dual-tier spinal clamp locking and retrieving system comprises a slotted clamp member, a tongued clamp member, and a clamp adjusting device. The slotted clamp member is composed of a hooked portion to hold a vertebra intended to be locked, a connecting portion, and a locking block having a through hole. The connecting portion or the locking block has one or more locking slots. The tongued clamp member is composed of a hooked portion to hold another vertebra intended to be locked, a connecting portion, and a tongue having thereon a locking block with a through hole. The tongue is dimensioned to fit into the locking slot of the slotted clamp member. The clamp adjusting device holds together the slotted clamp member and the tongued clamp member to effect a first tier locking mechanism. The tongue of the tongued clamp member is inserted into and held in the locking slot of the slotted clamp member so as to bring about a second tier locking mechanism.

6 Claims, 4 Drawing Sheets

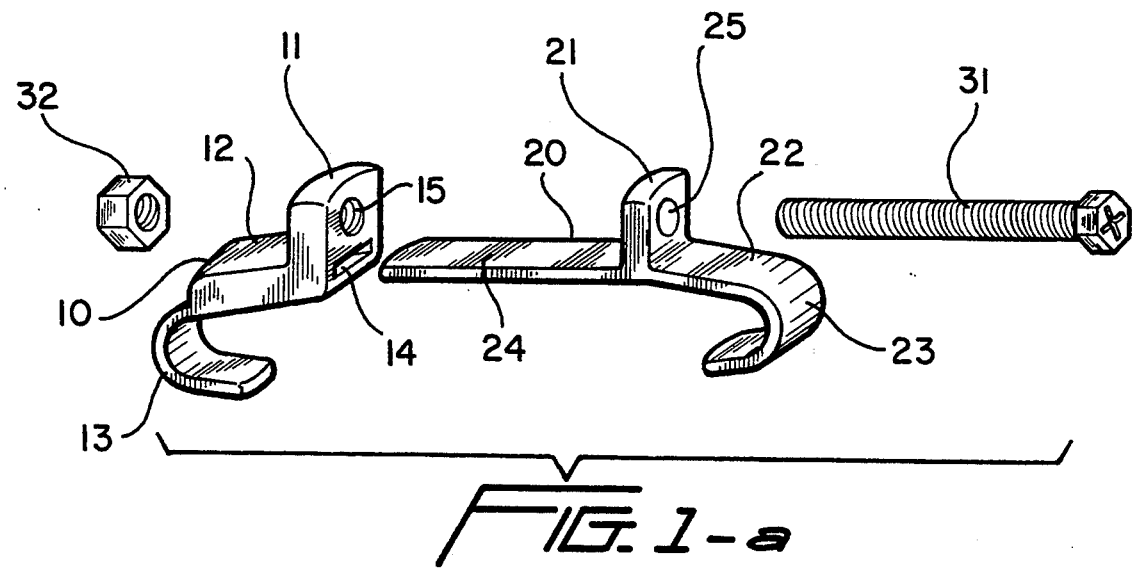
FIG. 1-a
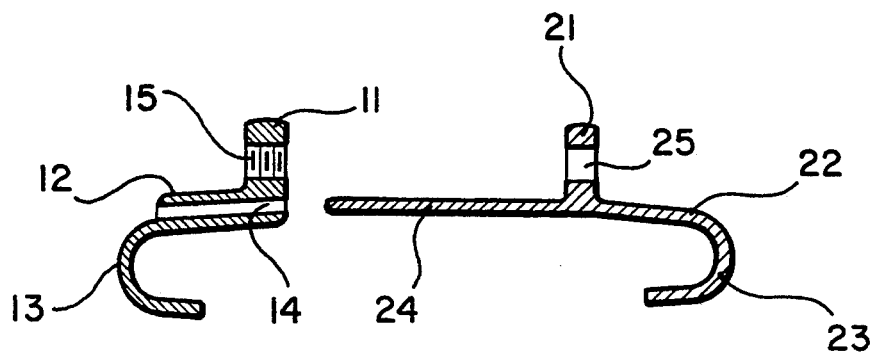
FIG. 1-b
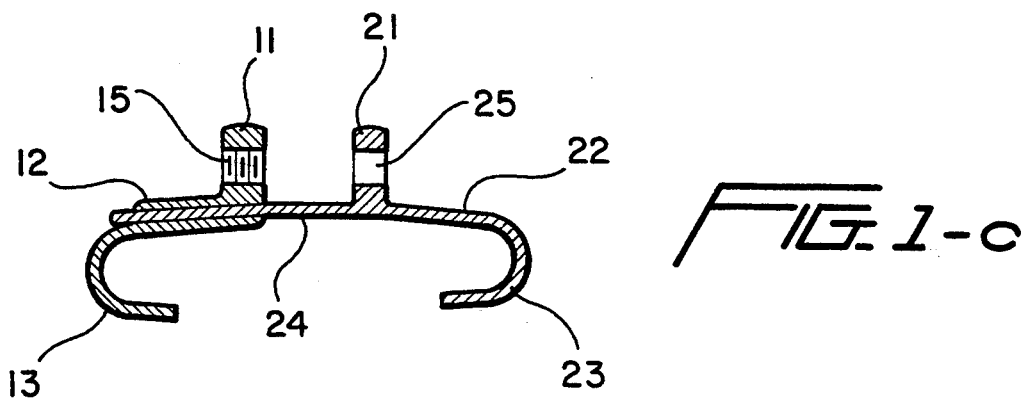
FIG. 1-c

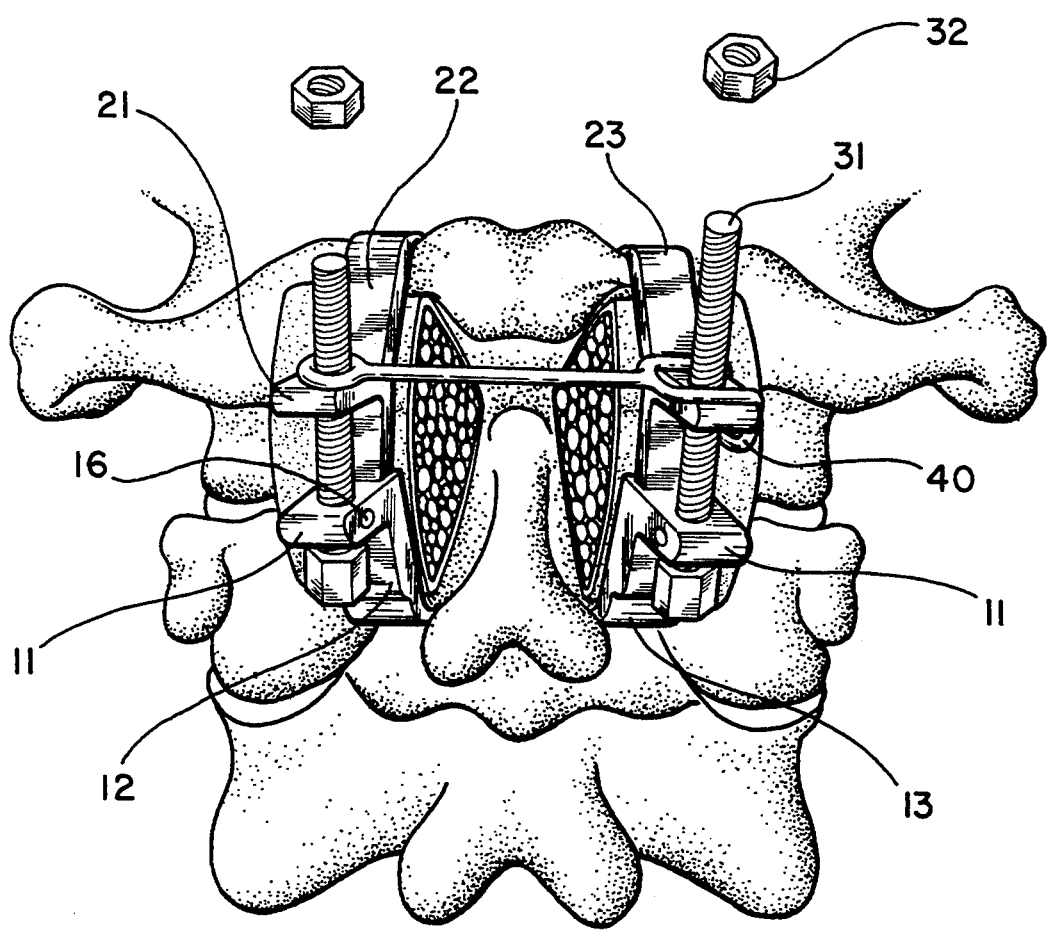
FIG. 2-a
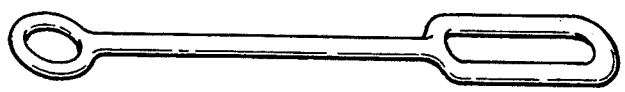
FIG. 2-b
FIG. 2-c

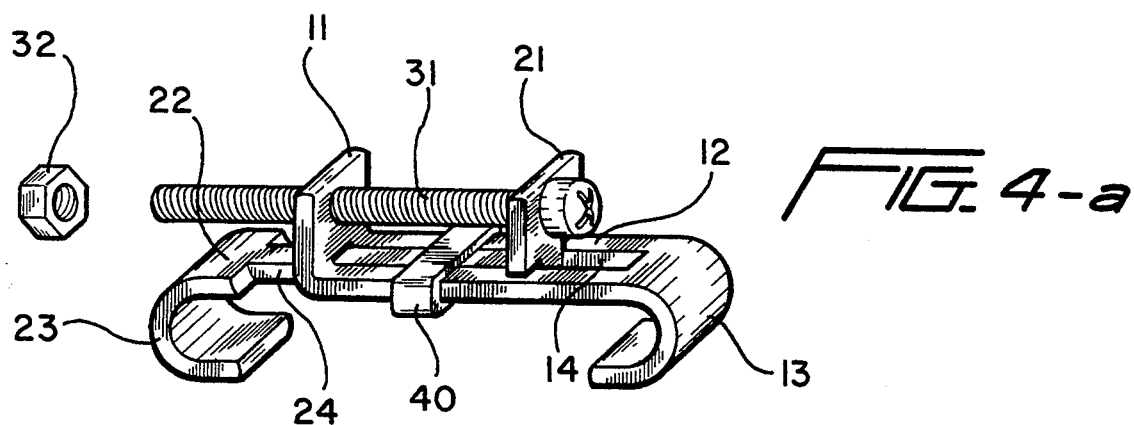
FIG. 4-a
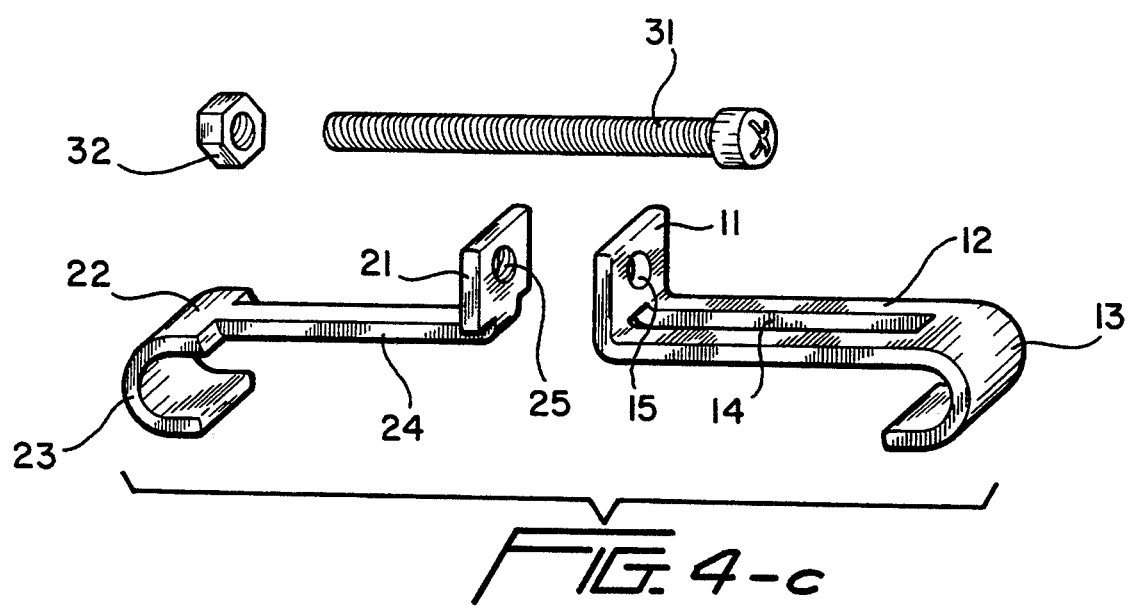
FIG. 4-c
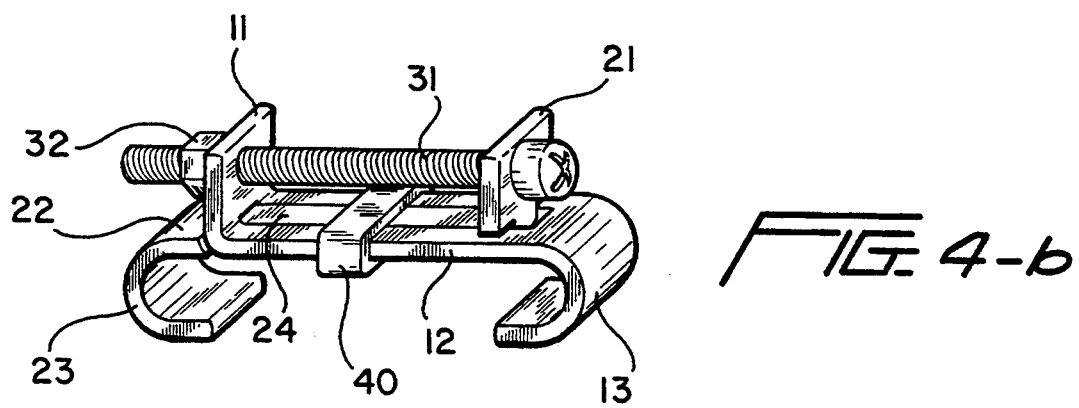
FIG. 4-b

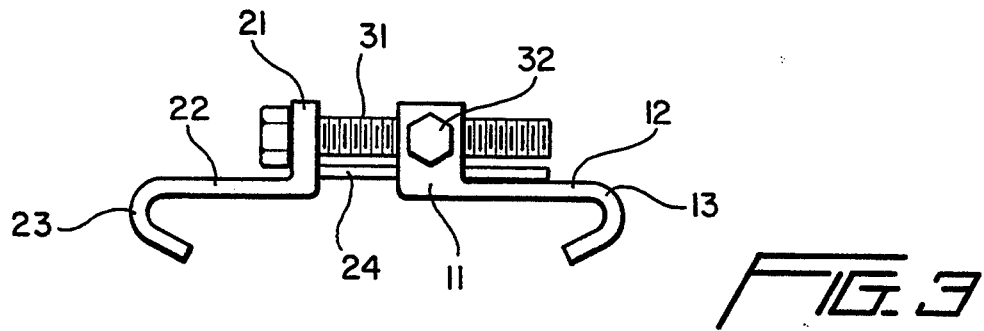
FIG. 3
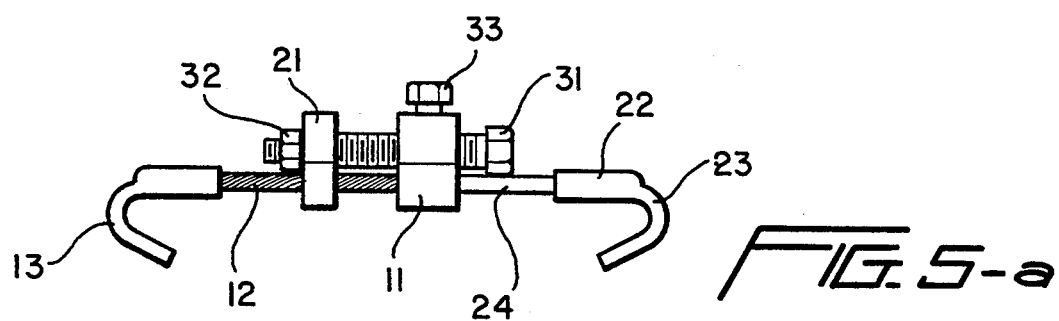
FIG. 5-a
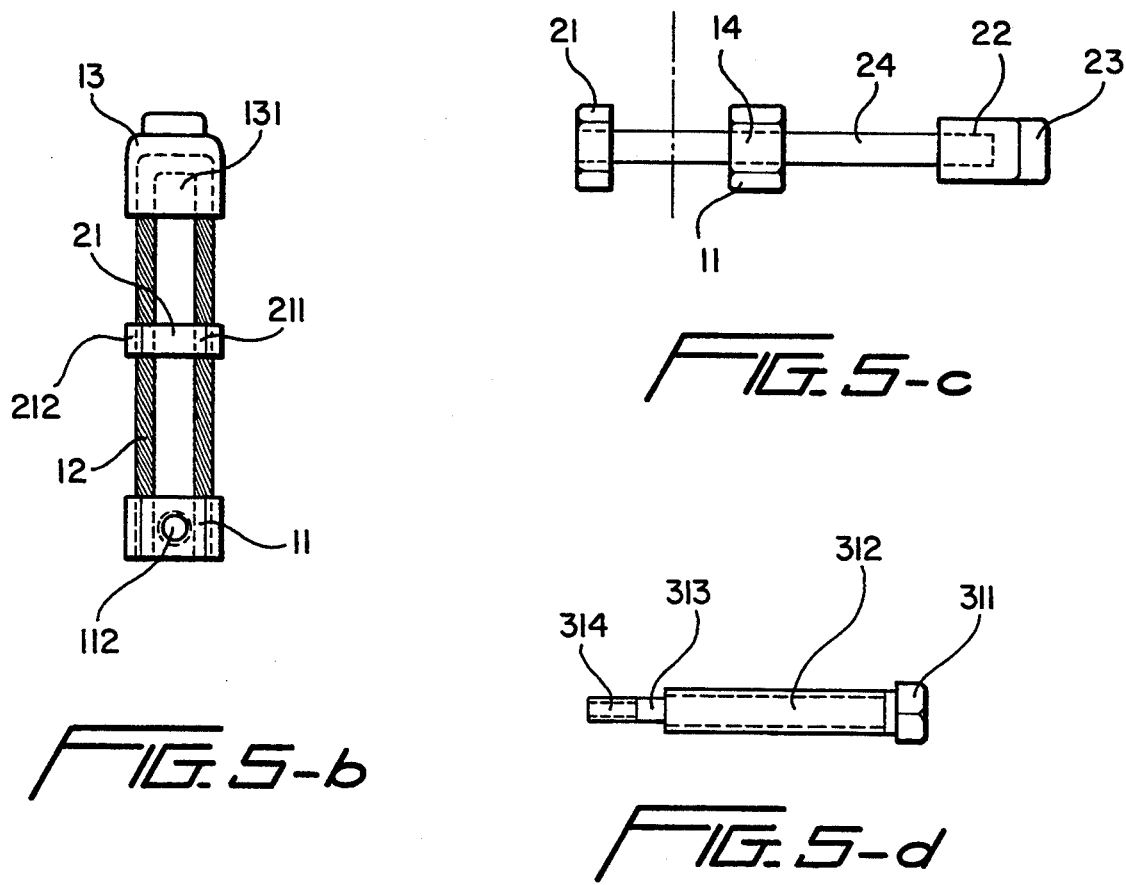
FIG. 5-b
FIG. 5-c
FIG. 5-d

DUAL-TIER SPINAL CLAMP LOCKING AND RETRIEVING SYSTEM

FIELD OF THE INVENTION

The present invention relates to a dual-tier spinal clamp locking and retrieving system.

BACKGROUND OF THE INVENTION

The dual-tier locking mechanism of the spinal clamp locking and retrieving system of the prior art is brought about by means of a nut and a bolt, which are used to fasten a pair of hooklike members holding a vertebra intended to be locked. The Halifax interlaminar clamp system made by the AME Corporation of the United States is a case in point. Such system is defective in design in that its dual locking effect is generally poor in view of the fact that various motions taking place between the vertebrae to be locked can often cause the fastening arrangement, such as the nut and the bolt, to become loosened to result in a total breakdown of the working order of the entire spinal clamp locking and retrieving system. Such shortcoming of the prior art system is also dealt with in an article entitled "Altantoaxial Arthrodesis Using Interlaminar Clamps" and published in the SPINE, 17 (3), 261 (1992) by Ronald Moskovich, et al. For more details, please refer to the FIG. 5 and the relevant text in the above-mentioned article.

SUMMARY OF THE INVENTION

It is therefore the primary objective of the present invention to provide a spinal clamp locking and retrieving system which is capable of effecting a dual-tier locking mechanism.

It is another objective of the present invention to provide a dual-tier spinal clamp locking and retrieving system, which is composed of a tongued clamp member, a slotted clamp member and a locking member.

In keeping with the principles of the present invention, the foregoing objectives of the present invention are attained by a dual-tier spinal clamp locking and retrieving system, which comprises a slotted clamp member, a tongued clamp member and a locking member.

The slotted clamp member is made up of a hooked portion, a connecting portion and a locking block. The hooked portion is curved inwards for use in holding a vertebra intended to be locked. The locking block is projected outwards and is provided with a through hole located near the center thereof. The connecting portion or the locking block has one or more locking slots.

The tongued clamp member is composed of a hooked portion, a connecting portion and a tongue having a locking block protruded outwards. The hooked portion is curved inwards for use in holding another vertebra intended to be locked. The locking block has one end situated on the tongue side and projected outwards. The locking block has a through hole located near the center thereof. The tongue is so dimensioned as to fit into the locking slot of the slotted clamp member.

The locking member is dimensioned to fit into the through holes of the locking blocks of the slotted clamp member and the tongued clamp member, so as to hold the slotted clamp member and the tongued clamp member together.

The dual-tier locking mechanism of the present invention is attained by the locking member and the tongued clamp member. The first tier locking mechanism is brought about by the locking member, which holds securely the slotted clamp member and the tongued clamp member by fitting into their through holes. The second tier locking mechanism is effected by the tongued clamp member which has the tongue dimensioned to fit into the locking slot of the slotted clamp member.

The foregoing objectives and features of the present invention will be better understood by studying the following detailed description of the preferred embodiments of the present invention in conjunction with the drawings provided herewith.

BRIEF DESCRIPTION OF THE DRAWINGS

FIG. 1-a shows an exploded view of a first preferred embodiment of the present invention.

FIG. 1-b is a sectional view of the first preferred embodiment of the present invention, showing that the tongue of the tongued clamp member has not been inserted into the locking slot of the slotted clamp member.

FIG. 1-c is a sectional view of the first preferred embodiment of the present invention, showing that the tongue of the tongued clamp member is held in the locking slot of the slotted clamp member.

FIG. 2-a is a schematic view of a second preferred embodiment of the present invention, showing that the system of the present invention holds the vertebrae intended to be locked.

FIG. 2-b is a schematic view of a horizontal locking device 40 as shown in FIG. 2-a.

FIG. 2-c is a schematic view of the horizontal locking device 40 that has been bent.

FIG. 3 shows a side elevational view of a third preferred embodiment of the present invention.

FIG. 4-a shows a perspective view of a fourth preferred embodiment in combination, according to the present invention.

FIG. 4-b is a schematic view of the fourth preferred embodiment of the present invention holding the vertebrae (not shown in the drawing).

FIG. 4-c shows an exploded view of the fourth preferred embodiment of the present invention, in which a check piece 40 is not labeled.

FIG. 5-a shows a perspective view of a fifth preferred embodiment of the present invention.

FIG. 5-b is a top view showing a manner by which the locking block of the tongued clamp member is coupled with the slotted clamp member, according to the fifth preferred embodiment of the present invention.

FIG. 5-c is a schematic view showing a manner by which the locking block of the slotted clamp member is coupled with the tongued clamp member, according to the fifth preferred embodiment of the present invention.

FIG. 5-d shows a schematic view of an adjusting screw of the fifth preferred embodiment of the present invention.

DETAILED DESCRIPTION OF THE PREFERRED EMBODIMENTS

Refering to FIGS. 1-a, 1-b, and 1-c, the first preferred embodiment of the present invention is shown to comprise a slotted clamp member 10, a tongued clamp member 20, and an adjusting screw 31.

The slotted clamp member 10 is composed of a locking block 11, a connecting portion 12 and a hooked portion 13. The connecting portion 12 is provided with a locking slot 14. The locking block 11 is furnished with a threaded hole 15. The tongued clamp member 20 is composed of a locking block 21, a connecting portion 22, a hooked portion 23, and a tongue 24. The locking block 21 is provided with a locking through hole 25. The adjusting screw 31 is provided with a nut 32. The adjusting screw 31 and the nut 32 form an adjusting device.

The locking block 11 of the slotted clamp member 10 is protruded in the direction away from a vertebra intended to be locked. The hooked portion 13 of the slotted clamp member 10 is curved toward the vertebra intended to be locked. Similarly, the locking block 21 of the tongued clamp member 20 is projected in the direction away from another vertebra intended to be locked. The hooked portion 23 of the tongued clamp member 20 is curved toward the another vertebra intended to be locked. The slotted clamp member 10 and the tongued clamp member 20 are held together by the adjusting screw 31 and the nut 32. The first tier locking mechanism of the present invention is brought about by the adjusting screw 31 which is so dimensioned as to fit into the threaded hole 15 of the slotted clamp member 10 and the locking through hole 25 of the tongued clamp member 20. The second tier locking mechanism of the present invention is effected by the tongue 24 of the tongued clamp member 20, which is inserted into and held in the locking slot 14 of the slotted clamp member 10.

The second preferred embodiment of the present invention is illustrated in FIG. 2-a, in which the definitions of the numerals designating the elements, such as 11, 12, 13, 21, 22, 23, 31 and 32, are corresponding to the definitions of those numerals which are used in the illustration of the first preferred embodiment. The second preferred embodiment is different from the first preferred embodiment in that the former is provided with a tongued clamp member having a locking block with a threaded hole, and a slotted clamp member having a block with a locking through hole. Therefore, the adjusting screw 31 is first put into the through hole of the locking block of the slotted clamp member before it engages the threaded hole of the locking block 21 of the tongued clamp member 20. As soon as the adjusting screw 31 is properly located in the threaded hole of the locking block 21, a horizontal locking device 40 is fitted over the adjusting screw 31, with the extra portion of the device 40 bending toward the dual-tier spinal clamp locking and retrieving system of the present invention. Thereafter, the nut 32 is fastened onto the adjusting screw 31. If necessary, a small screw (not shown in the drawing) may be screwed into a small threaded hole 16 located on a side of the locking block 11 of the slotted clamp member 10.

The third preferred embodiment of the present invention is illustrated in FIG. 3, in which the definitions of the numerals designating the elements, such as 11, 12, 13, 21, 23 and 31, are corresponding to the definitions of those numerals which are used in the illustration of the first preferred embodiment of the present invention. A small locking bolt 32 is used in the third preferred embodiment. The first preferred embodiment is different from the third preferred embodiment in that the latter has a slotted clamp member provided with a locking block with a locking slot. In other words, the tongue 24 is put through the locking slot adjacent to the connecting portion 12. In addition, the small locking bolt 32, which is fastened onto the side of the locking block 11, is used to replace the nut 32 of the first preferred embodiment, so as to ensure that the adjusting screw 31 is fastened securely to the locking block 11.

The fourth preferred embodiment of the present invention is illustrated in FIGS. 4-a, 4-b and 4-c. The slotted clamp member 10 is composed of a locking block 11 having a through hole 15, a connecting portion 12 having a locking slot 14, and a hooked portion 13. The tongued clamp member 20 comprises a locking block 21 having a threaded hole 25, a tongue 24, a connecting portion 22, and a hooked portion 21. The tongue 24 is slidably fitted into the locking slot 14. The adjusting screw 31 and the locking bolt constitute the clamp adjusting device. A check piece 40 is used to prevent the disengagement of the slotted clamp member 10 and the tongued clamp member 20. In addition, the use of the check piece 40 ensures that the tongue 24 slides with precision in the locking slot 14. The fourth preferred embodiment of the present invention differs from the first preferred embodiment of the present invention in that the former is provided with the tongue 24 which is located between the locking block 21 and the connecting portion 22, and that the former is provided with a connecting portion 12 having a locking slot 14 defined by two parallel plates making up the connecting portion 12, and further that the former is provided with the rotatable adjusting screw 31 which enables the hooked portions 13 and 23 of the slotted clamp member 10 and the tongued clamp member 20 to effect a clamping action in the direction toward the two vertebrae being held at such time when the locking blocks 11 and 21 of the slotted clamp member 10 and the tongued clamp member 20 slide in the direction away from the two vertebrae being held.

The fifth preferred embodiment of the present invention is illustrated in FIGS. 5-a through 5-d. A slotted clamp member 10 is composed of a locking block 11, two connecting cables 12 which is corresponding to the connecting portion 12 of the fourth preferred embodiment, and a hooked portion 13. Located between the two connecting points of the locking block 11 and the two connecting cables 12 is a locking slot 14, as shown in FIG. 5-c. The space between the two connecting cables 12 serves as a locking groove. The locking block 11 has a threaded hole. The tongued clamp member 20 is composed of a locking block 21, a tongue 24, a connecting portion 22 and a hooked portion 23. The tongued clamp member 20 of the fifth preferred embodiment is similar in structure to that of the fourth preferred embodiment. However, the fifth preferred embodiment of the present invention is provided with a through holes 211, 212 located at respective sides of the junction between the locking block 21 and the tongue 24 for receiving therein the connecting cable 12, as shown in FIG. 5-b. The locking block 21 has a through hole. The clamp adjusting device is composed of the adjusting screw 31 and the nut 32. The adjusting screw 31 has two different kinds of threads of two diameters, as shown in FIG. 5-d. The adjusting screw 31 is composed of a stopping nut 311, an adjusting threaded portion 312, a buffer portion 313, and a tail threaded portion 314 which engages a tail nut 32. The buffer portion 313 is just situated in the through hole of the locking block 21. The adjusting threaded portion 312 is intended to engage the threaded hole of the locking block 11. The rotation of the adjusting screw 31 triggers the locking block 11 to actuate the slotted clamp member 10 to move rightwards or leftwards, so as to adjust the gap between the slotted clamp member 10 and the tongued clamp member 20. As shown in FIG. 5-a, the union of the slotted clamp member 10 and the tongued clamp member 20 is further enhanced by a small locking screw 33, which is used to lock the adjusting screw 31 from the locking block 11. The method by which the locking block of the tongued clamp member is coupled with the slotted clamp member is illustrated in FIG. 5-b, in which the definitions of the numerals, such as 11, 12, 13, 14 and 21, are similar to the definitions of those numerals used in FIG. 5-a. The connecting cable 12 and the hooked portion 13 from a connecting zone 131. The locking block 21 is shown to comprise two through holes 211 and 212, each of which is so dimenstioned as to receive therein slidably the connecting cable 12. In addition, the locking block 11 is further provided with a small threaded hole 112 into which the locking screw 33 is screwed, as shown in FIG. 5-a. The locking block of the slotted clamp member is shown to be coupled with the tongued clamp member in FIG. 5-c, in which the definitions of the numerals, such as 11, 21, 22, 23 and 24 are the same as the definitions of those numerals used in FIG. 5-a. The locking block 11 is shown to comprise a locking slot 14 dimensioned to receive therein the tongue 24 of the tongued clamp member 20 such that the tongue 24 is free to slide in the locking slot 14.

All structural elements of the present invention are made of biocompatible materials suitable for the orthopedic surgery, such as the iron-based stainless steel 316 LVM, the Ti-6-4, the cobalt molybdenum chromiun alloy, etc.

The slotted clamp member of the present invention may be similar in construction to the Halifax system made by the AME Corporation, with the difference being that the present invention is provided with a locking slot which is located in the locking block or the connecting portion in such a manner that the locking slot is parallel to the surface of the connecting portion. If the locking slot is located in the connecting portion, the thickness of the plate making up the connecting portion of the present invention should be slightly greater than the thickness of the connecting plate of the Halifax system of the AME Corporation, so as to facilitate the construction of the locking slot in tho connecting portion. On the other hand, if the locking slot is located in the locking block of the present invention, the locking slot is preferably situated in such a manner that it is adjacent to the connecting portion and that it is oriented in the direction parallel to the surface of the connecting portion.

The tongued clamp member of the present invention may be similar in construction to the Halifax system of the AME Corporation. However, there is one major difference between the two systems, which is that the tongued clamp member of the present invention is provided with the tongue to be inserted into and held in the locking slot of the slotted clamp member.

The connecting portion of the slotted clamp member or the tongued clamp member of the present invention may be a flat boardlike construction similar to that of the Halifax system of the AME Corporation. However, the connecting poriton of the present invention may be made of a plurality of wires or wire ropes for connecting the hooked portion and the locking block of the slotted clamp member or for connecting the hooked portion and the locking block of the tongued clamp member. It is also suggested that a plurality of wires or wire ropes may be set up between the hooked portion and the connecting portion of the slotted clamp member and/or the tongued clamp member. When the connecting portion is constructed in the form of wires or wire ropes, or when the hooked portion and the connecting portion are connected by means of wires or wire ropes, the hooked portion may be so constructed that it has a plurality of hooks, each of which is in conjunction with one of the wires or the wire ropes. The wires referred to here are those which arc made up of untwisted strands while the wire ropes referred to are those which are composed of twisted strands. The use of the wires or the wire ropes as the connecting portion of the present invention is advantageous in that the hooked portion is permitted to hold a vertebra in various directions, positions and gripping points. Similarly, the use of wires or wire ropes as means to connect the hoked portion with the connecting portion is suggested. For more detail, please refer to the text on pages 20–25 in a book entitled "Operative Spinal Surgery" by Torrens and Dickson.

The clamp adjusting device of the present invention is similar in construction to the prior art devices, such as the Halifax system comprising a screw and a nut, the TSRH system of the Danex Corporation of the United States affording a three-point shear clamp mechanism, the ISOLA system of the Acromed Corporation of the United States providing an ISOLAR V-groove connection design, etc. The above-mentioned adjusting devices can be used to adjust the gap between the hooked portion of the slotted clamp member and the tongue of the tongued clamp member of the present invention. In addition, such adjusting devices are also effective in holding together the slotted clamp member and the tongued clamp member of the present invention so as to improve the efficiency of locking and retrieving the vertebrae.

It must be noted here that the system of the present invention is so designed that a horizontal adjusting device of the prior art can be incorporated into the present invention so as to reinforce the locking and retrieving effect of the present invention.

The embodiments of the present invention described above are to be regarded in all respects as merely illustrative and not restrictive. Accordingly, the present invention may be embodied in other specific forms without deviating from the spirit thereof. The present invention is therefore to be limited only by the scopes of the following appended claims.

What is claimed is:

1. A duel-tier spinal clamp locking and retrieving system, comprising:

a slotted clamp member composed of a first hooked portion bending toward a vertebra intended to be locked, a first connecting portion for connecting said first hooked portion with a first locking block, said first locking block protruding in a direction away from said vertebra and having a first through hole located near a center thereof, at least one of said first connecting portion and said first locking block having at least one locking slot;

a tongued clamp member composed of a second hooked portion bending toward another vertebra intended to be locked, a second connecting portion for connecting said second hooked portion with an elongated tongue which has thereon a second locking block projecting in a direction away from said another vertebra, said second locking block having a second through hole located near a center thereof, said tongue being so dimensioned as to fit deep into said at least one locking slot of said slotted clamp member; and a clamp adjusting device for adjustably holding together said slotted clamp member and said tongued clamp member, said clamp adjusting device connecting said first through hole of said slotted clamp member with said second through hole of said tongued clamp member;

wherein said clamp adjusting device holds together said slotted clamp member and said tongued clamp member to effect a first tier locking mechanism, and wherein said tongue of said tongued clamp member is inserted into and held in said at least one locking slot of said slotted clamp member so as to bring about a second tier locking mechanism.

2. The system according to claim 1 wherein said second locking block of said tongued clamp member is disposed between said tongue and said second connecting portion of said tongued clamp member.

3. The system according to claim 1 wherein said tongue of said tongued clamp member is arranged between said second locking block and said second connecting portion of said tongued clamp member.

4. The system according to claim 1 wherein at least one of said first connecting portion of said slotted clamp member and said second connecting portion of said tongued clamp member is subsequentially planar.

5. The system according to claim 1 wherein one of said first connecting portion of said slotted clamp member and said second connecting portion of said tongued clamp member is a connection cable.

6. The system according to claim 1 wherein one of said first connecting portion and said first hooked portion of said slotted clamp portion and said second connecting portion and said second hooked portion of said tongued clamp member are coupled with a connecting cable.

* * * * *